United States Patent [19]

Petersen

[11] Patent Number: 5,584,837
[45] Date of Patent: Dec. 17, 1996

[54] ACETABULAR CUP INSERTER FOR ORTHOPEDIC

[76] Inventor: Thomas D. Petersen, 9680 Alto Dr., La Mesa, Calif. 91941

[21] Appl. No.: 379,019

[22] Filed: Jan. 27, 1995

Related U.S. Application Data

[63] Continuation of Ser. No. 105,649, Aug. 13, 1993.

[51] Int. Cl.⁶ .................................................. A61B 17/58
[52] U.S. Cl. .................................. 606/91; 606/86; 606/99
[58] Field of Search .......................... 279/103; 16/114 R; 294/58; 403/292; 606/91, 99, 100, 86; 173/211, 210

[56] References Cited

U.S. PATENT DOCUMENTS

| | | | |
|---|---|---|---|
| 2,587,944 | 3/1952 | Williams | 173/211 |
| 3,144,736 | 8/1964 | Rusk et al. | 279/103 |
| 3,476,413 | 11/1969 | Coberly et al. | 403/292 |
| 4,305,394 | 12/1981 | Bertuch, Jr. | 606/91 |
| 4,475,549 | 10/1984 | Oh | 606/91 |
| 4,528,980 | 7/1985 | Kenna | 606/91 |
| 4,632,111 | 12/1986 | Roche | 606/91 |
| 4,716,894 | 1/1988 | Lazzeri et al. | 606/99 |
| 4,994,064 | 2/1991 | Aboczky | 606/91 |
| 5,061,270 | 10/1991 | Aboczky | 606/99 |
| 5,098,437 | 3/1992 | Kashuba et al. | 606/99 |
| 5,116,339 | 5/1992 | Glock | 606/91 |
| 5,284,483 | 2/1994 | Johnson et al. | 606/91 |
| 5,320,625 | 6/1994 | Bertin | 606/99 |

FOREIGN PATENT DOCUMENTS

535973  4/1993  United Kingdom ..................... 606/91

*Primary Examiner*—Jessica J. Harrison
*Assistant Examiner*—Michael O'Neill
*Attorney, Agent, or Firm*—H. Jay Spiegel

[57] ABSTRACT

Embodiments of an acetabular cup inserter include an elongated stem to which a handle is assembled in such a way that its orientation with respect to the stem may be adjusted 360°, that is, completely about the periphery of the stem. A buttress device is provided to engage the metal cup resiliently by use of an O-ring which prevents metal-to-metal contact avoiding fretting of the cup surface. The various embodiments disclosed include one embodiment wherein the buttress is axially aligned with the majority of the stem length as well as an embodiment wherein the axis of the buttress is parallel to and offset from the axis of the majority of the stem.

30 Claims, 4 Drawing Sheets

ACETABULAR CUP INSERTER FOR ORTHOPEDIC

This application is a continuation of application Ser. No. 08/105,649 filed Aug. 13, 1993.

BACKGROUND OF THE INVENTION

The present invention relates to embodiments of an acetabular cup inserter for orthopedic surgery. In the prior art, acetabular cup inserters are known. However, Applicant is unaware of any such device including all of the features and aspects of the present invention.

In performing hip replacement orthopedic surgery, several problems arise which, if not appropriately addressed, can result in post-surgical problems for the patient.

Firstly, in a typical surgical procedure, the surgeon will under ream the cavity in the acetabulum by 1 to 3 millimeters. Thereafter, the surgeon must orient the acetabular cup in a prescribed orientation allowing proper insertion of a screw in the superior outer quadrant to thereby mitigate possible damage to the blood vessels. Additionally, some manufacturers of hip prostheses require that the locking mechanism for the plastic cup insert must be superiorly orientated. These factors render hip replacement orthopedic surgery quite difficult where the gripping handle of the acetabular cup inserter has a fixed configuration. As such, a need has developed for an acetabular cup inserter including easy and reliable adjustment of the orientation of the gripping handle.

In a second aspect, as is known to those who practice orthopedic surgery, considerable pressure must be applied on the acetabular cup by the acetabular cup inserter to adjust the cup to the proper orientation and position. In known acetabular cup inserters, the inserter has a threaded end which is received within a threaded opening centrally located on the acetabular cup. As is known, the threads in a titanium-based cup will only resist approximately 20 foot-pounds of lateral pressure before deforming. Thus a need has developed for a buttress feature designed to supplement the threaded connection between the cup inserter and the cup to more uniformly spread the forces imposed upon the acetabular cup by the cup inserter. Such a buttress must take into account the wide variety of diameters of the acetabular cups which are now in use. Such cups may range in diameter from 36 millimeters up to 80 millimeters outer diameter. In addition, such a buttress must prevent metal-to-metal contact which causes fretting of the cup and creation of small particulate metal debris, resulting in osteolysis which can contribute to implant failure.

A further problem with acetabular cup inserters as they are presently known concerns the adaptability of one model of acetabular cup inserter to diverse manufacturers. Typically, each manufacturer utilizes a unique thread size, pitch and length and this fact makes it extremely difficult to make a basic instrument which may be applied to the acetabular cups of many manufacturers. As such, a need has developed for an acetabular cup inserter which may be made of a design which is universal concerning the acetabular cups of the diverse manufacturers.

Further, in some cases, due to certain surgical parameters which are caused by either extreme patient weight or the desire to utilize a small incision, an acetabular cup inserter having the buttress axially aligned with the predominant length of the stem thereof is not effective. As such, a need has developed for an acetabular cup inserter wherein the buttress thereof is offset from the axis of the predominant length of the stem.

The present invention, in its disclosed embodiments, has been developed with these surgical problems in mind.

SUMMARY OF THE INVENTION

The present invention relates to embodiments of an acetabular cup inserter for orthopedic surgery. The present invention includes the following interrelated objects, aspects and features:

(A) A first embodiment of the present invention includes an elongated stem having a distal end with a striking knob, a proximal end having a threaded recess and, approximately midway between the proximal and distal ends, a tapered portion which tapers in a direction of decreasing diameter from the distal end to the proximal end.

(B) A handle mount has an internal passageway which is tapered in correspondence to the tapered portion of the elongated stem so that the handle mount may be slid up the stem from the proximal end toward the distal end until an interference fit between the tapered portion and the tapered passageway through the handle mount causes the handle mount to become fixed in position. Proximal of the tapered portion on the stem, a threaded portion is provided which threadably receives a take-up nut designed to lock the axial and rotative positions of the handle mount in a desired configuration. In the preferred embodiments, the tapered portion of the stem and the tapered passageway through the handle mount have a taper of less than 6° so that the relationship between the tapered portion of the stem and the tapered passageway through the handle mount may be termed "self-locking". A rod emanates from the handle mount at an acute angle with respect to the proximal end of the elongated stem and terminates distally of the elongated stem with a handle which may be T-shaped. By loosening the take-up nut, the handle mount may be loosened and may be oriented at any rotative orientation with respect to the elongated stem whereupon the take-up nut may be tightened to lock the handle mount and, thereby, the handle in any such rotative position.

(C) The threaded recess in the proximal end of the elongated stem threadably receives the distal threaded end of an acetabular cup impactor. The cup impactor has a proximal end which is threaded with threads complementary to the threaded recess in a typical acetabular cup. Surrounding the distal end of the proximal threads of the cup impactor is a recess which receives an O-ring designed to engage the metal surface of the acetabular cup when the proximal threads are threaded into the threaded recess in the acetabular cup. When this occurs, the O-ring slightly flattens to provide a surface area of contact which buttresses the acetabular cup and prevents fretting of the surface thereof. The cup impactor of this embodiment of the present invention is specifically designed as a tip separate and apart from the elongated stem so that diverse tips having proximal threaded portions complementary to the various diverse types of acetabular cups may be suitably interconnected with the elongated stem to render this embodiment of the present invention usable in conjunction with the diverse types of acetabular cups which are now in the marketplace.

(D) A second embodiment of the present invention has numerous features in common with the first-mentioned embodiment. In this embodiment of the present invention, the elongated stem has a second set of peripheral threads proximal of the threads which receive the take-up nut. These threads have the same pitch and diameter as the threads designed to receive the take-up nut so that the take-up nut may be threaded over these proximal threads and, subsequently, over the take-up nut threads. These proximal threads are designed to receive a threaded recess at the distal end of a separate buttress device. In this embodiment, the elongated stem is also provided, at its proximal end, with threads complementary to the threaded recess in the acetabular cup. However, the separate buttress device may be threaded over the proximal threads of the elongated stem and, through rotations of the separate buttress device with respect to the stem, the position of extension or retraction of the proximal end of the buttress device carrying the O-ring may be adjusted with respect to the installed configuration of the threaded end of the elongated stem on the acetabular cup, so that the O-ring may be suitably flattened through such interengagement to provide the appropriate buttressing force. In this regard, the separate buttress device carries the O-ring on a proximal face thereof which is seen to taper in the distal direction of the separate buttress device from the axis thereof radially outwardly. This taper ensures maximum area engagement between the O-ring and the insert receiving surface of the acetabular cup while minimizing the possibility of metal-to-metal contact.

(E) In a further aspect, in conjunction with the teachings of the present invention, the metal face of the acetabular cup may be provided with a counterbore surrounding and of greater diameter with respect to the threaded recess thereof so that the O-ring engages the bottom of the counterbore which is flat. The flat nature of the bottom of the counterbore, as opposed to the natural curvature of the rest of the acetabular cup surface thereby precluding metal-to-metal contact therebetween.

(F) In a further aspect, as pointed out hereinabove in the BACKGROUND OF THE INVENTION, where it is desired to perform hip replacement surgery utilizing a small incision, or where the obesity of the patient requires, it is desirable to provide an acetabular cup inserter wherein the axis of the buttress is parallel to but offset from the axis of the elongated stem. As such, this structure is provided in a further embodiment of the present invention wherein the proximal end of the elongated stem is angled and has a fixture of U-shaped cross-section with an internal bore which is tapered at an angle of taper rendering the bore self-releasing. The buttress device is provided with a correspondingly tapered surface designed to releasably receive the bore in the U-shaped portion of the proximal end of the stem with the taper increasing in diameter in the proximal direction so that when the knob at the distal end of the elongated stem is struck, the tendency is to increase movement of the U-shaped portion of the proximal end of the handle proximally on the tapered surface of the buttress device. As assembled, the longitudinal axis of the buttress device is parallel to and offset from the longitudinal axis of the elongated stem.

As such, it is a first object of the present invention to provide embodiments of an acetabular cup inserter for orthopedic surgery.

It is a further object of the present invention to provide such a device including a gripping handle which may be adjusted at any position completely about the periphery of the associated elongated stem.

It is a still further object of the present invention to provide such a device including embodiments of a buttress device facilitating resilient surface area engagement between the acetabular cup inserter and the metal surface of the acetabular cup.

It is a still further object of the present invention to provide such a device including a further buttress device embodiment allowing adjustment of the axial position of the O-ring thereof with respect to the axial position of the proximal threaded end of the elongated stem.

It is a yet further object of the present invention to provide such a device including an embodiment wherein the buttress device is laterally offset from the elongated stem.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

With reference, first, to FIGS. 1–4, a first embodiment of the present invention is generally designated by the reference numeral 10 and is seen to include an elongated stem having a distal end 13 and a proximal end 15. Approximately midway between the proximal end and the distal end of the elongated stem 11, a tapered portion 17 is provided which tapers with decreasing area in the distal to proximal direction. Just proximal of the tapered portion 17, a threaded surface 19 is provided on the elongated stem 11, for a purpose to be described in greater detail hereinafter.

Figures 1, 2:
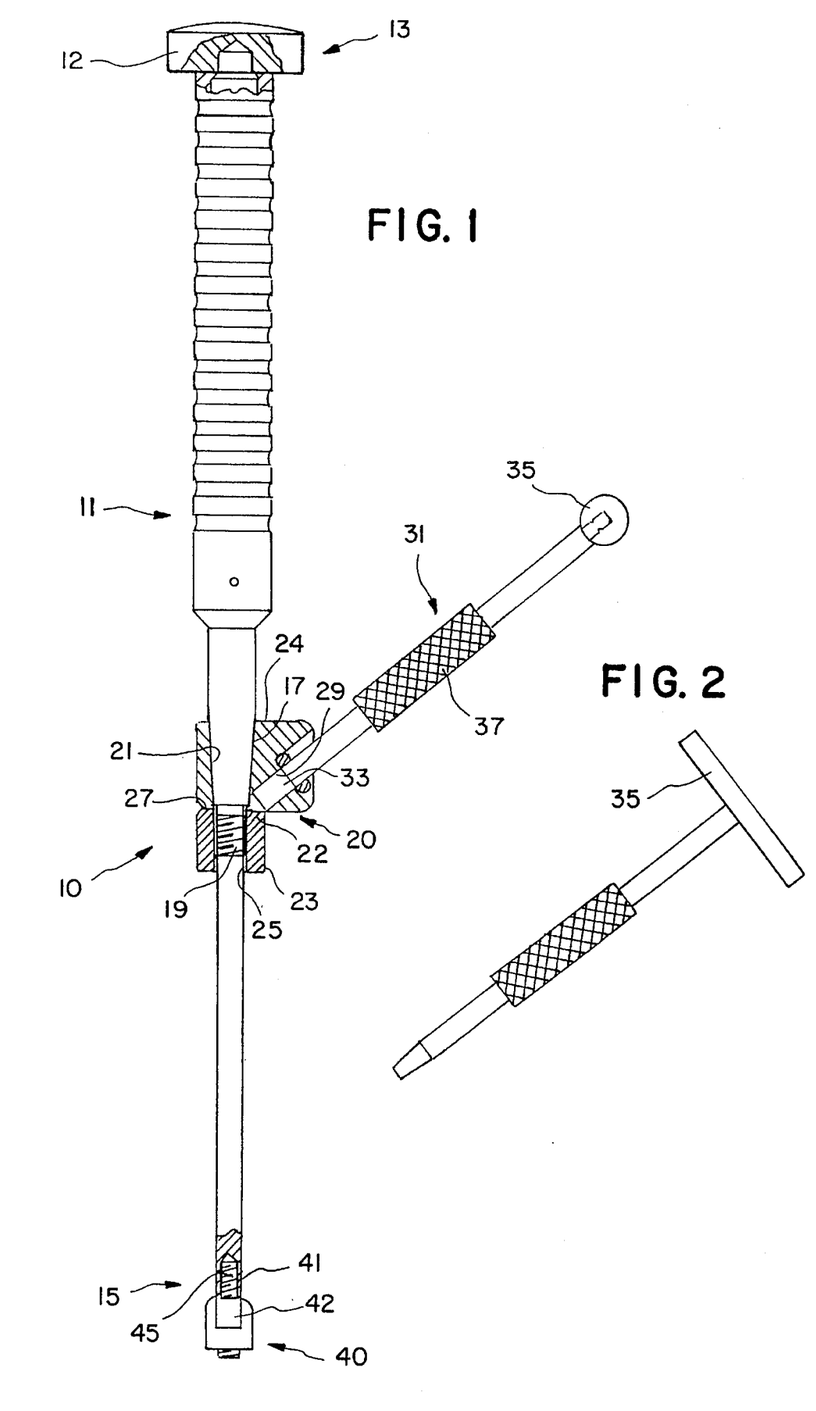
FIG. 1 shows a side view, partially in cross-section, of a first embodiment of an acetabular cup inserter.
FIG. 2 shows a further view of the handle portion shown in FIG. 1, but rotated 90° to show the T-shaped handle portion.

With further reference to FIG. 1, in particular, it is seen that fastening means for securing a handle 31 relative to the stem 11 includes a handle mount 20 including a tapered passageway 21 having a degree of taper corresponding to the degree of taper of the tapered portion 17 with the tapered passageway 21 and tapered portion comprising fastening means. In the preferred embodiment of the present invention, the tapered portion 17 and the tapered passageway 21 are tapered at an angle of less than 6°. As is well known in the art, tapers of less than 6° may be termed "self-locking" whereas tapers of greater than 6° may be termed "self-releasing". Thus, when the handle mount 20 is moved in the distal direction along the stem 11, eventually, the handle mount 20 will be locked in both axial and rotative positions with respect to the elongated stem 11.

The fastening means includes locking means having a take-up nut 23 including an internal threaded passageway 25 may be threaded over the threaded surface 19 of the elongated stem 11 until a distal end 27 thereof engages a proximal surface 22 of the handle mount 20 so that further rotations of the take-up nut 23 tending to move the take-up nut 23 in the distal direction of the elongated stem will move the handle mount 20 in the distal direction of the elongated stem 11 until such time as the handle mount 20 is wedged into a locked position both axially and rotatively. Rotation of the take-up nut 23 in the opposite direction causes the surface 27 thereof to disengage from the surface 22 of the handle mount 20 so that the handle mount 20 may be lightly tapped on the surface 24 thereof to release it from the tapered portion 17. Thereafter, the rotative position of the handle mount 20 with respect to the elongated stem 11 may be adjusted and, thereafter, the take-up nut 23 may be tightened against the surface 22 of the handle mount 20 to fix the axial and rotative positions thereof.

With particular reference to FIGS. 1 and 2, it is seen that the handle mount 20 has a tapered recess 29 sized to receive the tapered proximal end 33 of the handle 31 which also includes a distal cross-member 35 as well as an enlarged knurled surface sleeve 37 designed to permit gripping along with gripping of the cross-member 35. The degree of taper of the surfaces 29 and 33 is less than 6° so that the handle 31 may be inserted within the tapered passageway 29 with an interference locking fit. Moving the sleeve 37 upward disengages the handle 31 from the elongated stem 11.

Figure 3:
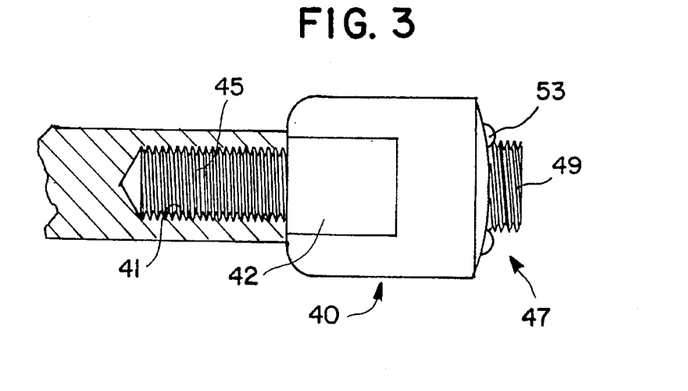
FIG. 3 shows a side view, partially in cross-section, of the cup impactor of this embodiment.
Figure 4:
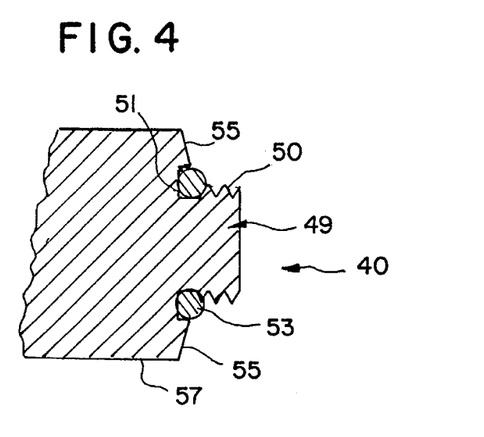
FIG. 4 shows a cross-sectional view through the proximal end of the cup impactor.

With further reference to FIGS. 1, 3 and 4, in particular, the proximal end 15 of the elongated stem 11 has a threaded recess 41 with threads complementary to the threaded distal end 45 of the cup impactor or cup attaching, buttressing and impacting device 40. Thus, the threaded distal end 45 of the cup impactor 40 may be threadably received within the threaded recess 41 at the proximal end 15 of the elongated stem 11 to mount the cup impactor 40 as shown in FIG. 1. In the preferred embodiment, the threads in the recess 41 and the threads on the distal end 45 are left hand threads as opposed to the right hand threaded portion 49. A flat 42 is provided on the impactor 40 to facilitate gripping with a wrench.

With particular reference to FIGS. 3 and 4, it is seen that the proximal end 47 of the cup impactor 40 includes a threaded portion 49 as well as a peripheral recess 51 distal to the termination of the threads 50 thereof. The recess 51 receives an O-ring 53 which may be made of any resilient material which will flatten when the threaded portion 49 is threadably received within the threaded recess of an acetabular cup. In the preferred embodiment of the present invention, the O-ring may be made of ethylene propylene. This material has been chosen because it may be successfully autoclaved and reused, it has the required resiliency described above, it has been found to be non-toxic to human tissues and the Food and Drug Administration has approved its use on instruments which touch human tissues during surgery. Any other material which similarly qualifies for use in this environment may be suitably employed. The recess 51 and O-ring 53 comprise buttressing means.

With particular reference to FIG. 4, it is seen that the depth of the recess 51 is slightly greater than ½ the thickness of the O-ring 53. This configuration is provided to ensure retention of the O-ring 53 in its mounted position as shown in FIG. 4. As also seen in FIG. 4, a tapered surface 55 is provided which extends radially outwardly from the recess 51 to the side wall 57 of the impactor 40. This tapered surface 55 is provided to preclude metal-to-metal engagement between the surface 55 and the metal surface of the acetabular cup.

With the above description in mind, the operation of the embodiment of FIGS. 1–4 in the performance of orthopedic surgery, in particular, in the insertion of the acetabular cup should be self-evident. The cup impactor 40 which is complementary to the particular acetabular cup to be employed is suitably attached to the proximal end 15 of the elongated stem 11. The threaded end 49 of the cup impactor 40 is suitably threaded into the threaded recess formed in the acetabular cup until such time as the O-ring 53 engages the metal surface of the acetabular cup so that further rotation of the acetabular cup with respect to the threaded portion 49 causes the proximal surface of the O-ring 53 to flatten thereby providing a surface area of buttressing contact between the impactor 40 and the acetabular cup.

The take-up nut 23 is loosened and the rotative orientation of the handle mount 20 with respect to the elongated stem 11 is suitably adjusted. Thereafter, the take-up nut 23 is tightened to fix the rotative and axial positions of the handle 31 with respect to the elongated stem 11 and, thereby, the particular position of the acetabular cup. Thereafter, the knob 12 is suitably impacted on a striking surface thereof while the handle 31 is gripped to cause installation of the acetabular cup. Thereafter, mounting screws may be inserted in the acetabular cup as is well known to those skilled in the art. If necessary, to facilitate such installation, the take-up nut 23 may be loosened and the handle 31 may be rotated to a position which does not interfere with such installation.

Figure 5:
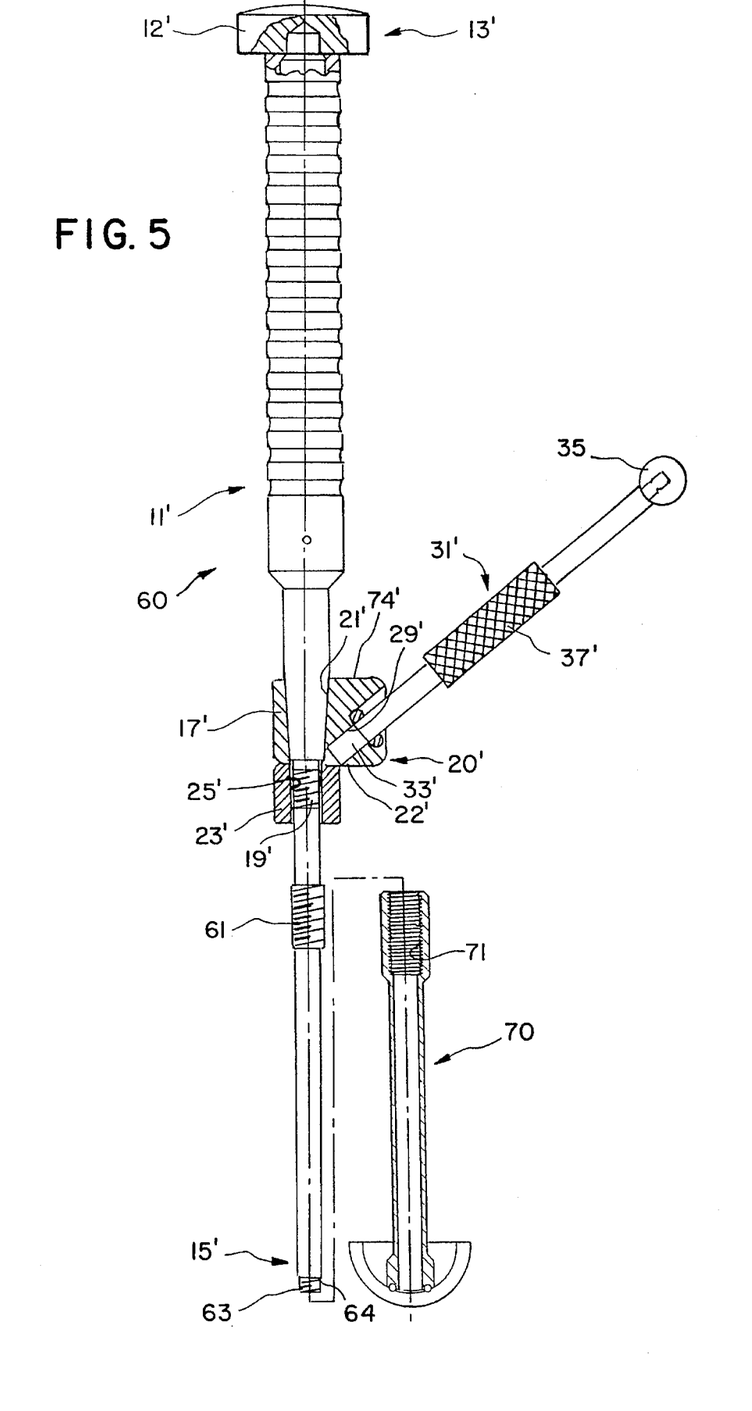
FIG. 5 shows a side view, partially exploded and partially in cross-section of a second embodiment of the present invention.
Figure 6:
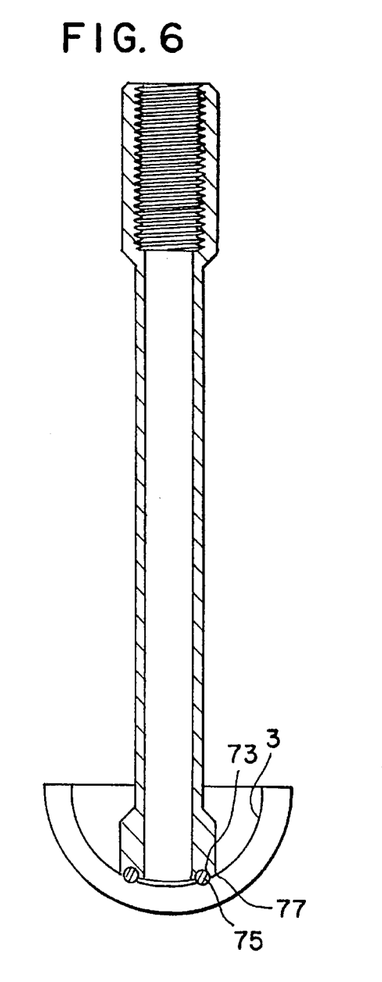
FIG. 6 shows an enlarged cross-sectional view of the buttress device of the embodiment of FIG. 5.

Reference is now made to FIGS. 5 and 6 wherein a further embodiment of the present invention is shown. In describing the embodiment of FIGS. 5 and 6, like elements from the embodiment of FIGS. 1–4 will be described using like primed reference numerals.

With reference to FIGS. 5 and 6, the acetabular cup inserter 60 is seen to include an elongated stem 11' having a distal end 13' and a proximal end 15'. Between the proximal and distal ends of the elongated stem 11', a tapered surface 17' is provided which is complementary to the tapered passageway 21' of the handle mount 20'. The handle mount 20' also includes a tapered passageway 29' designed to receive the tapered proximal end 33' of the handle 31' which also includes the cross-member 35' as well as the enlarged knurled surface sleeve 37' permitting the handle 31' to be easily gripped. The handle mount includes the surfaces 22' and 24' for the same purposes as described above with respect to the embodiment of FIGS. 1–4.

The elongated stem 11' also includes the threaded surface 19' which is complementary to the threads 25' of the take-up nut 23'. At the distal end 13' of the elongated stem 11', the knob 12' is suitably provided.

All of the above-described features are the same as in the embodiment of FIGS. 1–4. The device 60 differs from the device 10 illustrated in FIGS. 1–4 as including the further provision of a threaded surface 61 proximal to the threaded surface 19', however, having threads of equal pitch and diameter so that the take-up nut 23' may be threaded over the threaded surface 61 and thence over the threaded surface 19'. At the proximal end 15' of the elongated stem 11', a further threaded surface 63 is provided which is designed to be threadably received within the threaded opening of an acetabular cup.

The embodiment of FIGS. 5 and 6 includes the further provision of a separate buttressing device 70 which includes a distal threaded recess 71 having threads complementary to the threaded surface 61 as well as a proximal recess 73 (FIG. 6) sized to receive the O-ring 75. The surface of the proximal end of the buttressing device 70 radially outward from the recess 73 and designated by the reference numeral 77 is tapered in the same manner as the surface 55, best illustrated in FIG. 4, to preclude metal-to-metal engagement between the buttressing device 70 and the surface 3 of the acetabular cup 1 (FIG. 6). As should be understood from FIG. 5, in particular, when the buttressing device 70 is suitably mounted over the proximal end 15' of the elongated stem 11', the axial position of the O-ring 75 may be suitably adjusted with respect to the particular position of the threaded proximal end 63. In this way, with the buttressing device 70 completely threaded over the threaded surface 61 to leave the threaded proximal end 63 of the elongated stem 11' completely exposed, the threaded proximal end 63 of the elongated stem 11' may be completely threaded onto the acetabular cup 1 until the shoulder 64 thereof engages about the periphery of the threaded recess (not shown) of the acetabular cup, or bottoms out into the threaded cup recess frequently seen in smaller cups. Thereafter, the buttressing device 70 may be rotated so that the O-ring 75 moves proximally of the elongated stem 11' and into engagement with the surface 3 of the acetabular cup 1 whereupon further such rotations of the buttressing device 70 will cause the O-ring 75 to flatten providing a resilient area of contact between the buttressing device 70 and the surface 3 of the acetabular cup 1, while the surfaces 77 of the buttressing device 70 preclude metal-to-metal contact therebetween.

As described above, through manipulations of the take-up nut 23', the rotative position of the handle 31' may be suitably adjusted and the knob 12' may be suitably impacted to facilitate installation of the acetabular cup 1.

Figures 7, 8, 9:
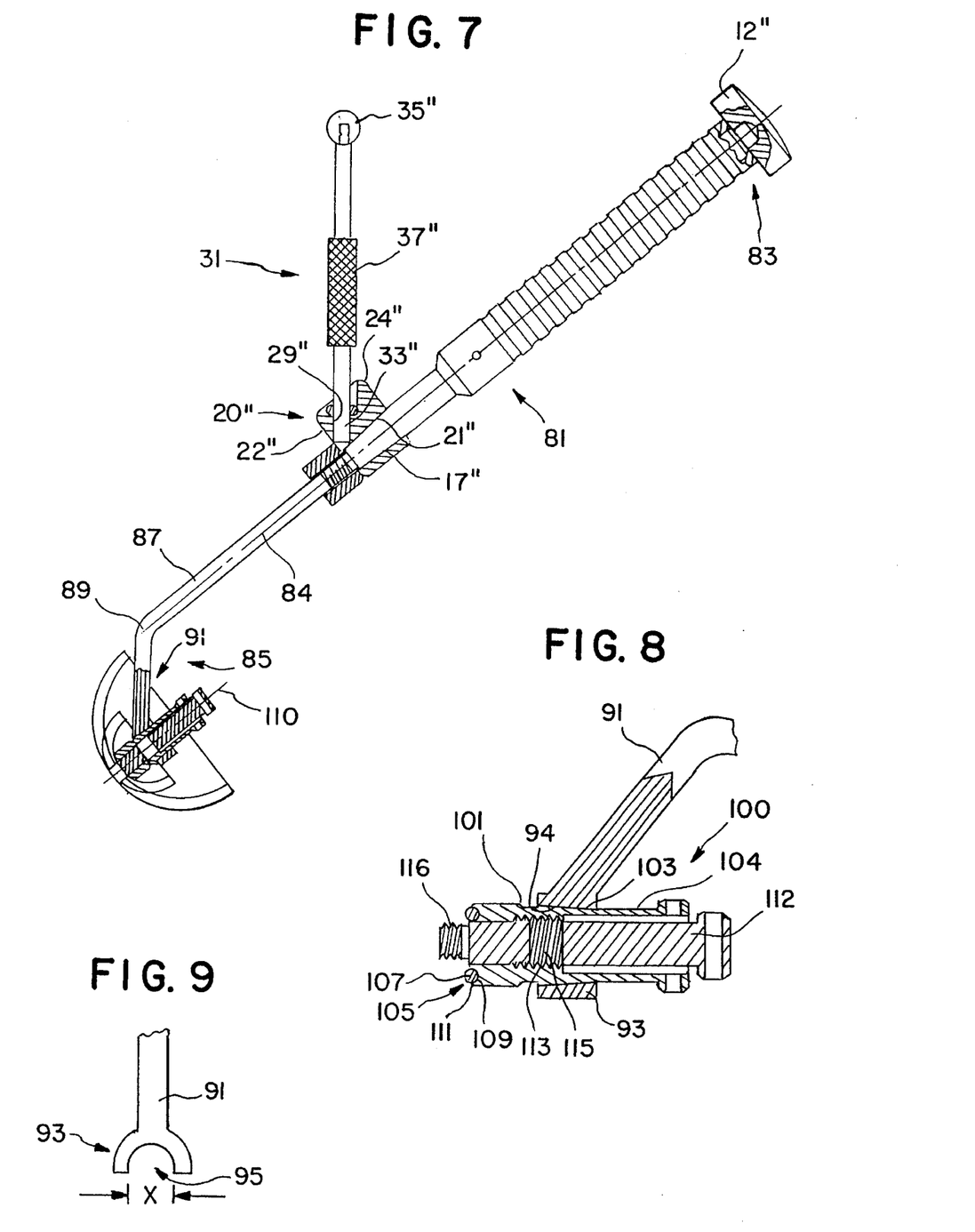
FIG. 7 shows a side view, partially in cross-section, of a further embodiment of the present invention.
FIG. 8 shows an enlarged cross-sectional view of the proximal end of the device illustrated in FIG. 7.
FIG. 9 shows an end view of the proximal end of the elongated stem of the embodiment of FIGS. 7 and 8.

Reference is now made to FIGS. 7–9 so that a description of a third embodiment of the present invention may be made. This third embodiment of the present invention is generally designated by the reference numeral 80 and like features from the embodiments of FIGS. 1–6 will be described using like double-primed reference numerals.

With reference to FIGS. 7–9, the inventive inserter 80 is seen to include an elongated stem 81 having a distal end 83 and a proximal end 85. Between the proximal and distal ends of the stem 81, a tapered surface 17" is provided which is complementary to the tapered passageway 21" of the handle mount 20", which handle mount also includes the surfaces 22" and 24". The handle mount 20" also has the tapered recess 29" configured to receive the tapered proximal end 33" of the handle 31" which also has the cross-member 35" and the enlarged diameter knurled surface sleeve 37".

As particularly shown in FIG. 7, the proximal end 85 of the elongated stem 81 includes a straight portion 87 and a bend 89 leading to a proximal termination 91 having a U-shaped terminus 93 (FIG. 9) having an opening 95 having a width "X" as shown in FIG. 9. This width "X" is provided for a purpose to be described in greater detail hereinafter.

With particular reference to FIG. 8, a cup impactor 100 includes a sleeve 101 having an outer central tapered surface 103 designed to receive the tapered passageway 94 of the distal terminus 93. The tapered surface 103 and the tapered passageway 94 are preferably tapered at an angle of greater than 6° so that they are self-releasing. That is, after impacting has been completed, the impactor 100 may be removed from the elongated stem 81 without the need to apply a great deal of force. The proximal end 105 of the impactor 100 includes a recess 109 sized to receive the O-ring 107. The surface 111 radially outward from the recess 109 is tapered in the distal direction with decreasing diameter to preclude metal-to-metal contact between the impactor 100 surface 111 and the acetabular cup.

On the impactor 100, distally of the tapered surface 103 is a cylindrical surface 104. The dimension "X" of the opening 95 of the terminus 93 is sized to be slightly larger than the diameter of the surface 104 so that the terminus 93 opening 95 may be inserted laterally over the surface 104 and, thereafter, the terminus 93 may be moved proximally over the impactor 100 so that the surfaces 94, 103 interengage to fixedly mount the terminus 93 on the impactor 100.

As should be understood, with reference to FIG. 7, in particular, the longitudinal axis 110 of the impactor 100 is parallel to the axis 84 of elongation of the stem 81 but laterally spaced therefrom. As described hereinabove, the embodiment designated by the reference numeral 80 is most suitably employed in the performance of hip replacement surgery where either a small incision is desired or the obesity of the patient so necessitates.

FIG. 7 shows two acetabular cups, in phantom, to demonstrate the versatility of the inventive device.

With further particular reference to FIG. 9, it is seen that the sleeve 101 includes a threaded region 113 with threads complementary to the threaded surface 115 of the rod 112. At the proximal end of the rod 112, a threaded portion 116 is provided with threads complementary to the threaded recess in the acetabular cup.

As should be understood from FIGS. 7–9, the threaded proximal end 116 of the rod 112 may be threaded into the threaded recess of the acetabular cup. Thereafter, the sleeve 101 may be rotated with respect to the rod 112 to advance the O-ring 107 into engagement with the metal surface of the acetabular cup. Thereafter, the U-shaped end 93 of the stem 81 may be placed over the surface 104 and thereafter advanced over the tapered surface 103 thereof to mount the impactor 100 as shown in FIG. 8. Thereafter, impact on the knob 12" is operative to install the acetabular cup at the surgical site.

Figure 10:
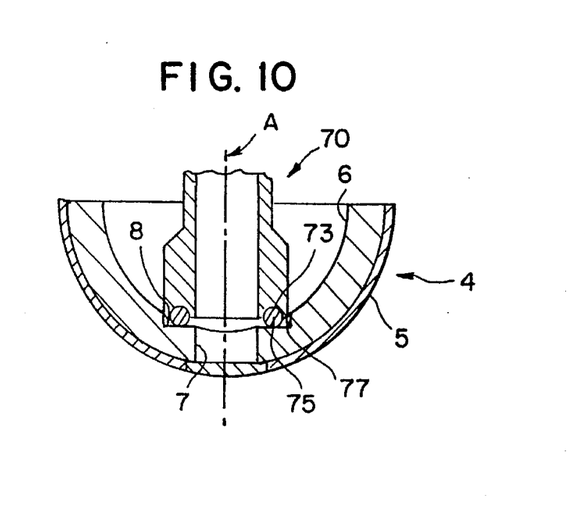
FIG. 10 shows an enlarged cross-section depicting a modification in the metal face of the acetabular cup.

With reference, now, to FIG. 10, a modification in the acetabular cup will now be described.

FIG. 10 shows the proximal end of the buttressing device 70 including the recess 73, O-ring 75 and lateral wall 77. The acetabular cup 4 includes an outer periphery 5 and an inner periphery 6. A centrally located bore 7 is provided to receive the threaded proximal end of the cup impactor. A relieved portion 8 having a shoulder 9 is formed in the surface 6 with the portion 8 lying perpendicular to the axis A of the bore 7. The relieved portion 8 provides a flat surface for receipt of the O-ring 75 of the buttressing device 70. In this way, metal-to-metal contact between the buttressing device 70 and the acetabular cup 4 is precluded.

As should be understood from FIG. 4, without the relieved portion 8, the O-ring 75 would confront an arcuate surface, leading to the possibility that the edges of the surfaces 77 of the device 70 could engage the surface 6 thereby causing fretting of the surface 6 and subsequent osteolysis. The relieved portion 8 precludes such fretting.

In the method of performing surgery in accordance with the teachings of FIG. 10, prior to using the device 10, 60 or 80, the relieved portion 8 is reamed or otherwise formed in the surface 6 of the acetabular cup 4.

As such, an invention has been disclosed in terms of preferred embodiments thereof as well as methods of use which fulfill each and every one of the objects of the invention as set forth hereinabove and provide a new and useful acetabular cup inserter for orthopedic surgery of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. An acetabular cup inserter, comprising an elongated stem having a proximal end and a distal end, said proximal end being adapted for connection to a prosthetic acetabular component, a handle extending outwardly from the elongated stem and being rotatable about the stem, and fastening means for securing the handle relative to the stem, said fastening means including a generally smooth conical surface on said stem engageable with a generally smooth correspondingly tapered conical passageway through the handle to fasten said handle in any one of an infinite number of rotative positions about a circumference of said stem.

2. The inserter of claim 1, wherein said fastening means includes locking means proximal of said handle for releasably wedging said tapered conical passageway onto said conical surface to fix a rotative position of said handle with respect to said stem.

3. An acetabular cup inserter, comprising:

a) an elongated stem having a proximal end and a distal end;

b) a handle mount on said stem between said proximal end and distal end, said handle mount carrying a handle;

c) fastening means for releasably fastening said handle mount in any one of an infinite number of rotative positions about a circumference of said stem, said fastening means comprising a smooth conical surface on said stem, a correspondingly tapered smooth conical passageway through said handle mount, and locking means for moving said handle mount with respect to said stem to lock said handle mount in any of said rotative positions;

d) a striking surface on said distal end of said stem; and e) an acetabular cup attaching, buttressing and impacting device on said proximal end of said stem including resilient buttressing means for preventing fretting of an acetabular cup to which said inserter may be attached.

4. The inserter of claim 3, wherein said handle is removably attachable to said handle mount.

5. The inserter of claim 1, wherein said conical surface is tapered from a larger diameter to a smaller diameter in a direction from said distal end to said proximal end, said locking means being located on said elongated stem proximal of said tapered surface.

6. The inserter of claim 5, wherein said locking means comprises a threaded surface on said stem proximal of said conical surface and a lock nut with threads complementary to said threaded surface, said lock nut being movable over said threaded surface and thereby engaging a proximal surface of said handle mount to move said handle mount distally on said stem to thereby wedge said conical passageway onto said conical surface.

7. The inserter of claim 3, wherein said striking surface is located on a knob mounted on said distal end.

8. The inserter of claim 3, wherein said acetabular cup attaching, buttressing and impacting device includes attaching means for attaching said inserter to an acetabular cup, said attaching means comprising an attachment member having first coupling structure complementary to second coupling structure on an acetabular cup.

9. The inserter of claim 8, wherein said first coupling structure comprises a threaded surface, a second coupling structure comprising a threaded passageway through an acetabular cup having threads complementary to said first coupling structure threaded surface.

10. The inserter of claim 9, wherein said first coupling structure is directly formed on said proximal end of said stem.

11. The inserter of claim 9, wherein said attaching, buttressing and impacting device comprises a separate member attachable on said proximal end of said stem.

12. The inserter of claim 11, wherein said stem proximal end has a threaded recess, said separate member having a distal threaded stem having threads complementary to said threaded recess whereby said separate member may be releasably attached on said proximal end of said stem.

13. The inserter of claim 10, further including a buttressing sleeve mountable on said stem proximal end.

14. The inserter of claim 13, wherein said stem proximal end includes an angled bend whereby said buttressing sleeve is laterally offset from said stem distal end.

15. The inserter of claim 14, wherein said sleeve has a tapered outer surface, said stem proximal end having a U-shaped terminus with a tapered inner surface complementary thereto.

16. The inserter of claim 13, wherein said buttressing means is formed on a proximal surface of said sleeve.

17. The inserter of claim 16, wherein said buttressing means comprises an O-ring partially recessed in a groove in said proximal surface.

18. The inserter of claim 12, wherein said buttressing means comprises a recess in a proximal surface of said separate member and an O-ring partially recessed in said proximal surface recess.

19. The inserter of claim 13, wherein said buttressing sleeve has a threaded recess threadably received on a threaded sleeve receiving surface on said stem spaced distally of said proximal end of said stem.

20. The inserter of claim 18, wherein acetabular cup threads are surrounded by a flat recessed area facing said stem when said stem is coupled thereto, said O-ring engaging said flat recessed area.

21. The inserter of claim 1, wherein said buttressing means includes an O-ring captured and partially recessed in a groove.

22. The inserter of claim 21, wherein said groove is laterally spaced radially outwardly from an axis of elongation of said buttressing means.

23. The inserter of claim 22, further including a tapered surface surrounding said groove.

24. The inserter of claim 21, wherein said O-ring protrudes outwardly from said groove.

25. In an acetabular cup inserter including an elongated stem having a proximal end and a distal end, said distal end having a striking surface, said proximal end having attachment means for attaching said acetabular cup inserter to an acetabular cup at an attachment location thereon, the improvement comprising buttressing means surrounding said attachment means for preventing fretting of a surface of an acetabular cup to which said inserter may be attached, said buttressing means comprising a recess in said proximal end of said stem capturing and partially recessing an O-ring received therein, said recess preventing lateral movement of said O-ring with respect to said proximal end.

26. The inserter of claim 25, wherein said recess comprises an annular recess.

27. The inserter of claim 25, wherein said recess has a depth slightly greater than one-half a thickness of said O-ring.

28. The inserter of claim 25, wherein said O-ring is made of ethylene propylene.

29. The inserter of claim 25, wherein said proximal end includes a separate member attachable on said stem and carrying said buttressing means.

30. An acetabular cup inserter, comprising:

a) an elongated stem having a proximal end and a distal end;

b) a handle mount on said stem between said proximal end and distal end, said handle mount carrying a handle;

c) fastening means for releasably fastening said handle mount in any one of an infinite number of rotative positions about a circumference of said stem, said fastening means comprising a tapered surface on said stem, a correspondingly tapered passageway through said handle mount, and locking means for engaging said handle mount to lock said handle mount in any of said rotative positions;

d) a striking surface on said distal end of said stem; and e) an acetabular cup attaching, buttressing and impacting device on said proximal end of said stem including resilient buttressing means including an O-ring captured and partially recessed in a groove for preventing fretting of an acetabular cup to which said inserter may be attached.

* * * * *